United States Patent
Klose

(10) Patent No.: US 9,047,659 B2
(45) Date of Patent: Jun. 2, 2015

(54) SYSTEM, METHOD AND COMPUTER-ACCESSIBLE MEDIUM FOR PERFORMING ATTENUATION-CORRECTED MULTISPECTRAL LUMINESCENCE TOMOGRAPHY OF CERENKOV AND BIOLUMINESCENT LIGHT SOURCES

(75) Inventor: Alexander Klose, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 169 days.

(21) Appl. No.: 13/695,227

(22) PCT Filed: Apr. 28, 2011

(86) PCT No.: PCT/US2011/034342
§ 371 (c)(1),
(2), (4) Date: Dec. 18, 2012

(87) PCT Pub. No.: WO2011/137247
PCT Pub. Date: Nov. 3, 2011

(65) Prior Publication Data
US 2013/0108132 A1    May 2, 2013

Related U.S. Application Data

(60) Provisional application No. 61/330,224, filed on Apr. 30, 2010.

(51) Int. Cl.
G06K 9/00 (2006.01)
A61B 5/103 (2006.01)
(Continued)

(52) U.S. Cl.
CPC ............ *G06T 7/0012* (2013.01); *A61B 5/0035* (2013.01); *A61B 5/0073* (2013.01); *A61B 5/0261* (2013.01); *A61B 5/055* (2013.01); *A61B 5/14551* (2013.01)

(58) Field of Classification Search
USPC .......................... 382/131, 154; 600/476, 587
See application file for complete search history.

(56) References Cited

U.S. PATENT DOCUMENTS 5,905,261 A     5/1999  Schotland et al.
8,676,302 B2 *  3/2014  Wang et al. .................. 600/476
(Continued)

OTHER PUBLICATIONS

International Search Report for International Patent Application No. PCT/US2011/034342, Apr. 28, 2011.
(Continued)

*Primary Examiner* — Sheela Chawan
(74) *Attorney, Agent, or Firm* — Andrews Kurth LLP

(57) ABSTRACT

The present disclosure can provide apparatus, system, methods, and computer-accessible medium for generating particular information which is at least one of three-dimensional information or intensity information of a tissue portion which can include at least one of a tissue surface or a tissue volume. For example, the exemplary method can include determining a light intensity distribution of light provided on the tissue portion, using the light intensity distribution, determining one or more attenuation maps of the tissue portion, obtaining one or more multispectral measurements of the light intensity distribution on the tissue portion taken from one or more views, and generating the particular information using an image reconstruction procedure in conjunction with data from the one or more tissue attenuation maps and the multispectral measurements.

24 Claims, 10 Drawing Sheets

(51) Int. Cl.
*G06T 7/00* (2006.01)
*A61B 5/00* (2006.01)
*A61B 5/026* (2006.01)
*A61B 5/055* (2006.01)
*A61B 5/1455* (2006.01)

(56) References Cited

U.S. PATENT DOCUMENTS

| | | | |
|---|---|---|---|
| 2005/0004446 A1* | 1/2005 | Cowan et al. | 600/407 |
| 2005/0143965 A1* | 6/2005 | Failla et al. | 703/2 |
| 2007/0093700 A1* | 4/2007 | Wang et al. | 600/317 |
| 2007/0238957 A1* | 10/2007 | Yared | 600/407 |
| 2008/0039715 A1* | 2/2008 | Wilson et al. | 600/424 |
| 2010/0009747 A1 | 1/2010 | Reville et al. | |

OTHER PUBLICATIONS

International Written Opinion for International Patent Application No. PCT/US2011/034342, Apr. 28, 2011.

\* cited by examiner

SYSTEM, METHOD AND COMPUTER-ACCESSIBLE MEDIUM FOR PERFORMING ATTENUATION-CORRECTED MULTISPECTRAL LUMINESCENCE TOMOGRAPHY OF CERENKOV AND BIOLUMINESCENT LIGHT SOURCES

CROSS REFERENCE TO PRIOR APPLICATIONS

This application relates to and claims the benefit of priority to International Patent Application No. PCT/US11/034342 filed on Apr. 30, 2011, and from U.S. Provisional Application Ser. No. 61/330,224, filed on Apr. 30, 2010, which is incorporated by reference herein in its entirety.

STATEMENT REGARDING FEDERALLY SPONSORED RESEARCH

This invention was made with government support under Grant Nos. 5U54CA126513-029001 and 4R33CA118666 awarded by the National Institutes of Health. The government has certain rights in the invention.

FIELD OF THE DISCLOSURE

The present disclosure relates to exemplary embodiments of computer accessible-medium, methods and systems for providing a luminescent tomography, and more particularly, exemplary embodiments of computer accessible-medium, methods and systems for providing a luminescent tomography of Cerenkov and bioluminescent light sources in biological structures.

BACKGROUND INFORMATION

Luminescence imaging of living animals can be shown to be a useful technique for obtaining information on both normal and diseased biological processes taking place in that particular animal. The images can generally be obtained with low light level charge-coupled device ("CCD") cameras or other sensitive optical imaging devices, and the biological process can be visualized using luminescent reporters which are produced by or which target some compound (e.g., an enzyme, protein, etc.), or some cell surface receptor which can be part of the process. The images generally show regions of optical emission which can be correlated with the biological process. Sources of visible light emission can either be nuclear reporter probes as a source for Cerenkov light or a luciferase-luciferin reporter system as a source for bioluminescent light.

A source of light emission can be provided by a Cerenkov luminescence reporter system, in which Cerenkov radiation can be emitted when a charged particle (e.g., an electron or positron), passes through a medium, such as biological tissue, with a speed greater than the speed of light in the same medium. The charged particle can disrupt the local electromagnetic field of the medium by displacing the electrons of the atoms. Radiation can be emitted when the displaced electrons fall back into an equilibrium state. Beta minus (i.e., electrons) or beta plus (i.e., positrons) radiation above the threshold velocity (i.e., energy>200 keV), which is generated by the decay of nuclear reporter probes in biological tissue, can produce Cerenkov radiation at wavelengths of visible light. The light can be detected with a sensitive optical camera and, hence, functions as an optical reporter signal for beta minus/plus nuclear reporter probes (e.g., fluoro-D-deoxyglucose) in nuclear imaging.

Further, the Cerenkov light in the visible and near-infrared is typically strongly scattered in biological tissue. Therefore, planar or two-dimensional (2D) images of Cerenkov radiation at the tissue surface obtained with current imaging technology typically contain little information about the actual depth and strength of the light emitting beta radiation, i.e., nuclear reporter probe. Hence, tomographic imaging technology is generally needed to retrieve three-dimensional (3D) information about the "true" reporter probe distribution and source of Cerenkov radiation. Such technology can facilitate quantitative imaging of nuclear reporter probes via Cerenkov radiation.

A source of light emission can also be provided by a bioluminescent luciferase/luciferin reporter system, in which a target of interest can be transfected with a luc gene that expresses the enzyme luciferase at the target site. A substrate, luciferin, can be administered to the animal and can be distributed throughout the animal tissue. The enzyme luciferase can catalyze a chemoluminescent reaction of luciferin at the target site, which can result in light emission with a range of wavelengths between 500 and 700 nm. Light at these wavelengths, however, is typically multiply scattered in the tissue and, thus, diffuse light distributions on the tissue surface can be measured with 2D planar imaging techniques. Hence, no direct image of the bioluminescent reporter probe's location or emission strength can typically be obtained. Moreover, light absorption by tissue chromophores, such as (oxy-)hemoglobin, significantly attenuate the optical signal. Therefore, without tomographic reconstruction, which can take the scattering and absorption effects into account, accurate determination of absolute light emission levels is generally not feasible.

Luminescence tomography has the potential to overcome the limitations of planar luminescence imaging and can provide precise spatial location and emission strength of light emission levels of reporter probes within the tissue. In luminescence tomography, 2D luminescence images can be used together with a light propagation model and a reconstruction procedure that retrieves the 3D source distribution. The light propagation model, also termed forward problem, can be generally based on partial-differential equations (PDE) for the photon flux inside the tissue. These PDEs can be solved with numerical techniques, which can calculate the boundary current of light on the tissue surface for a given set of optical parameters and source points inside the tissue. The image reconstruction procedure can solve the inverse source problem determining the source location and strength inside the tissue domain given the planar luminescence images taken on the domain boundary. The inverse problem can be both highly ill-posed due to strong light scattering and can be underdetermined due to the limited boundary measurement data. Moreover, there can be errors in the modeled light propagation solution owing to the uncertainty in the optical tissue properties, which are known to vary in their spectral optical properties. These properties are often determined from ex vivo measurements that may not be representative of the in vivo conditions.

Accordingly, it may be beneficial to address at least some of the issues and/or problems described herein above.

SUMMARY OF EXEMPLARY EMBODIMENTS OF THE DISCLOSURE

At least some of the above described problems can be addressed by exemplary embodiments of the computer-accessible medium, methods and systems according to the present disclosure.

According to one of the exemplary embodiments of the present disclosure, a computer-accessible medium, method and system for obtaining three-dimensional information of a tissue surface can be provided, comprising calculating a light intensity distribution of light provided on a tissue surface, using the light intensity distribution, determining one or more attenuation maps of the tissue, obtaining one or more multispectral measurements of the light intensity distribution on the tissue surface taken from one or more views, and solving an image reconstruction method using data from the one or more tissue attenuation maps and the multispectral measurements, to provide three-dimensional information of the tissue surface.

According to exemplary embodiments of the present disclosure, a method can be provided for generating particular information which is at least one of three-dimensional information or intensity information of a tissue portion which can include at least one of a tissue surface or a tissue volume. For example, a light intensity distribution of light provided on the tissue portion can be determine, and using the light intensity distribution, one or more attenuation maps of the tissue portion can be determined. Further, one or more multispectral measurements of the light intensity distribution on the tissue portion taken from one or more views can be obtained, and using a computer arrangement, the particular information can be generated using an image reconstruction procedure in conjunction with data from the one or more tissue attenuation maps and the multispectral measurements. The tissue portion can include a curved tissue surface and the particular information can include at least one a source power density, a source distribution in three-dimensional space, or a concentration distribution. Additionally, the light intensity distribution can be determined for a given set of point sources or a known distribution of sources on the curved tissue surface. Further, the attenuation maps of the tissue portion can be represented by absorption and scattering coefficients of the tissue. The one or more attenuation maps of the tissue portion can be determined by at least one of: (a) a light propagation model, (b) a parameter optimization technique, or (c) a give source distribution.

According to some exemplary embodiments of the present disclosure, the light intensity distribution can be determined using a light propagation model, which can include at least one of a radiative transfer procedure, a simplified spherical harmonics procedure or a diffusion procedure. The simplified spherical harmonics procedure can include a diffusion equation that can be solved using at least one of a finite-difference procedure, a finite volume procedure or a finite element procedure. Further, the solved procedure can include a utilization of at least one of structured grids with equidistant grid points that define a domain of the tissue volume or unstructured grids with irregular grid point separations which define a domain of the tissue volume.

According to certain exemplary embodiments of the present disclosure, it is also possible to reconstruct a source distribution by (a) determining a light propagation model, (b) the one or more attenuation maps of the tissue volume, and/or (c) a linear image reconstruction procedure.

In further exemplary embodiments of the present disclosure, a computer-accessible medium having instructions thereon can be provided for generating particular information which is at least one of three-dimensional information or intensity information of a tissue portion which can include at least one of a tissue surface or a tissue volume. For example, when a hardware processing arrangement executes the instructions, the computing arrangement can be configured to determine a light intensity distribution of light provided on the tissue portion, using the light intensity distribution, determine one or more attenuation maps of the tissue portion, obtain one or more multispectral measurements of the light intensity distribution on the tissue portion taken from one or more views, and generate the particular information using an image reconstruction procedure in conjunction with data from the one or more tissue attenuation maps and the multispectral measurements. The tissue portion can include a curved tissue surface and the particular information can include at least one a source power density, a source distribution in three-dimensional space, or a concentration distribution. Additionally, the light intensity distribution can be determined for a given set of point sources or a known distribution of sources on the curved tissue surface. Further, the attenuation maps of the tissue portion can be represented by absorption and scattering coefficients of the tissue. The attenuation map(s) of the tissue portion can be determined by at least one of: (a) a light propagation model, (b) a parameter optimization technique, or (c) a give source distribution.

According to some exemplary embodiments of the present disclosure, the light intensity distribution can be determined using a light propagation model, which can include at least one of a radiative transfer procedure, a simplified spherical harmonics procedure or a diffusion procedure. The simplified spherical harmonics procedure can include a diffusion equation that can be solved using at least one of a finite-difference procedure, a finite volume procedure or a finite element procedure. Further, the solved procedure can include a utilization of at least one of structured grids with equidistant grid points that define a domain of the tissue volume or unstructured grids with irregular grid point separations which define a domain of the tissue volume.

According to still further exemplary embodiments of the present disclosure, a system can be provided for generating particular information which is at least one of three-dimensional information or intensity information of a tissue portion which can include at least one of a tissue surface or a tissue volume. For example, the exemplary system can include a computer-accessible medium having instructions thereon, when a hardware processing arrangement executes the instructions, the computing arrangement can be configured to determine a light intensity distribution of light provided on the tissue portion, using the light intensity distribution, determine one or more attenuation maps of the tissue portion, obtain one or more multispectral measurements of the light intensity distribution on the tissue portion taken from one or more views, and generate the particular information using an image reconstruction procedure in conjunction with data from the one or more tissue attenuation maps and the multispectral measurements. According to certain exemplary embodiments, the exemplary system can include an electromagnetic radiation source arrangement configured to provide the light.

The tissue portion can include a curved tissue surface and the particular information can include at least one a source power density, a source distribution in three-dimensional space, or a concentration distribution. Additionally, the light intensity distribution can be determined for a given set of point sources or a known distribution of sources on the curved tissue surface. Further, the attenuation maps of the tissue portion can be represented by absorption and scattering coefficients of the tissue. The one or more attenuation maps of the tissue portion can be determined by at least one of: (a) a light propagation model, (b) a parameter optimization technique, or (c) a give source distribution.

According to some exemplary embodiments of the present disclosure, the light intensity distribution can be determined using a light propagation model, which can include at least one of a radiative transfer procedure, a simplified spherical harmonics procedure or a diffusion procedure. The simplified spherical harmonics procedure can include a diffusion equation that can be solved using at least one of a finite-difference procedure, a finite volume procedure or a finite element procedure. Further, the solved procedure can include a utilization of at least one of structured grids with equidistant grid points that define a domain of the tissue volume or unstructured grids with irregular grid point separations which define a domain of the tissue volume.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
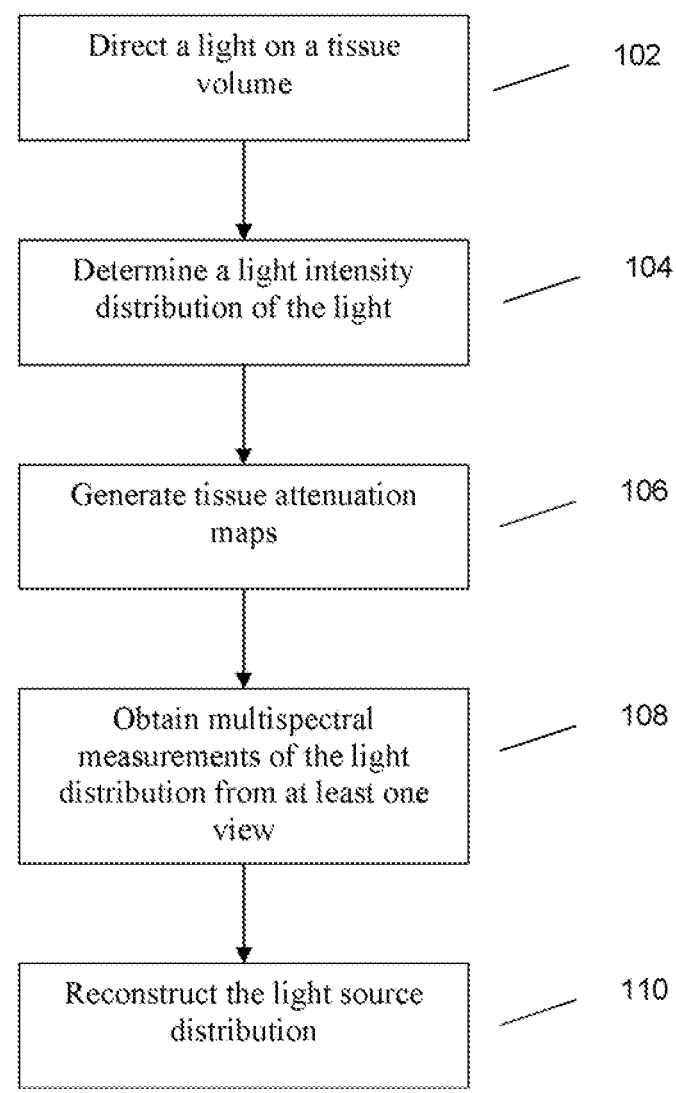
FIG. 1 is an exemplary flow diagram of an exemplary method according to certain exemplary embodiments of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular exemplary embodiments illustrated in the figures.

DETAILED DESCRIPTION OF EXEMPLARY EMBODIMENTS OF DISCLOSURE

A. Exemplary Luminescence Tomography

An exemplary embodiment of a luminescence tomography method according to the present disclosure can be provided that can utilize a simplified spherical harmonics of the Nth order (e.g., $SP_N$ with N=1, 3, 5, 7, ...) procedure, including, e.g., a diffusion equation ($SP_1$), to determine a light intensity distribution on a curved tissue surface for a given set of point sources inside the tissue. As shown in FIG. 1, an exemplary embodiment of the present disclosure can provide a method 100 for generating information, e.g., a reconstruction of a light source distribution. The exemplary method can include, for example, directing a light on a tissue volume (102), determining a light intensity distribution of the light (104), generating tissue attenuation maps (106) obtaining multispectral measurements of the light distribution from at least one view (108), and reconstructing the light source distribution (110).

The exemplary $SP_N$ solutions, for example, can be accurate for luminescent sources located close to the tissue surface and for short wavelengths less than 640 nm with a relatively strong light absorption $\mu_a$>0.5 cm$^{-1}$ inside the tissue. These are conditions under which the diffusion model can be shown to be inaccurate. The $SP_N$ equations can be solved with a finite-difference (FD) method by using regular grids with equidistant grid points for defining the tissue domain. The curved geometry of the tissue surface can be taken into account with a blocking-off region procedure, where the tissue surface geometry can be approximated by grid points closest to the actual surface. The blocking-off procedure on regular grids can have benefits when compared to procedure for unstructured grids with nonequidistant grid points in that computational overhead is present because of the regular grid structure.

Further, unknown tissue attenuation maps can be determined, which can be represented by the absorption and scattering coefficients of the tissue, for different wavelengths of the luminescent reporter probe spectrum. The unknown uniform attenuation maps can be determined, for example, by using the light propagation model (e.g., a blocking-off $SP_N$ procedure), a global parameter optimization technique (e.g., an evolution strategy), and a given source distribution (e.g., a laser diode or white light source with a filter placed on a tissue surface).

An exemplary sought source distribution can be reconstructed using a light propagation model (e.g., the $SP_N$ method), prior calculated attenuation maps (e.g., absorption and scattering coefficients), and a linear image reconstruction procedure (e.g., algebraic reconstruction technique, expectation-maximization method, conjugate gradient solver for matrix equations).

Multispectral measurements of the luminescence light distribution on the tissue surface taken from different views (e.g., ventral and dorsal views) of an animal can be used. Additionally, the luminescence light on the tissue surface can be co-registered prior to luminescence image reconstruction with CT and MR images of the same animal taken while in a fixed pose. This co-registration strategy can have several advantages. For example, such exemplary strategy can facilitate the use of non-uniform attenuation maps for luminescence image reconstruction where different tissue types are segmented by the CT/MR images. The identified tissue types or organs can be assigned differing absorption and scattering coefficients provided by an empirical function leading to non-uniform attenuation maps. Further, the MRI/CT co-registration can also provide an anatomical reference enabling more accurate interpretation of the luminescence tomography derived functional information.

The light propagation model (e.g., $SP_N$ equations, diffusion equation) and the image reconstruction method (e.g., EM method, ART, etc.) can be solved on a multi-processor environment entailing, e.g., a personal computer (PC) which can be, e.g., one or more of: (1) a multi-core central processing unit (CPU) or several CPUs, or (2) a graphics processing unit (GPU) or several GPUs. Such exemplary method described above can be suited for GPUs and lead to speed-up factors of 20 to 30 when compared to a CPU.

A1 Exemplary Light Propagation Model

In an exemplary embodiment of a luminescent source reconstruction process according to the present disclosure, the partial boundary current, $J^+$, at D detector points located on the tissue surface for a given set $\{Q_1, \ldots, Q_m, \ldots, Q_M\}$ of M sources and known optical tissue parameters can be calculated. The exemplary optical parameters can be represented by the scattering, $\mu_s$, and the absorption coefficient, $\mu_a$, which can be a function of wavelength. The exemplary interior sources, $Q_m$, can be defined as point sources, where each source can pertain to an image voxel of the image reconstruction domain. The partial boundary current, $J^+$, which can be calculated by the light propagation model, can then become input to the inverse source model, as described in further detail herein below.

The functional relationship between $J^+$, $Q_m$, $\mu_s$, and $\mu_a$ can be given by a light propagation model F, e.g.:

$$J^+ = F(Q_m, \mu_s, \mu_a). \quad (1)$$

In general, F can be based either on the equation of radiative transfer (ERT) or on one of its approximations. For example, the ERT can be given by an integro-differential equation for the angular photon flux, $\psi$, of luminescence light, e.g.:

$$\Omega \cdot \nabla \psi(r, \Omega, \lambda) + \mu_t(r, \lambda) \psi(r, \Omega, \lambda) = \mu_s(r, \lambda) \int_{4\pi} p(\Omega \cdot \Omega') \psi(r, \Omega', \lambda) d\Omega' + Q_m(r, \lambda) \quad (2)$$

$\psi$ can be a function of the spatial location r, direction $\Omega$, and wavelength $\lambda$. The attenuation coefficient, $\mu_t$, with units of $cm^{-1}$, can be the sum of $\mu_a$ and $\mu_s$. The phase function $p(\Omega, \Omega')$ can be the distribution function for photons anisotropically scattering from direction $\Omega'$ into the differential solid angle $d\Omega$ around direction $\Omega$. A commonly-applied phase function in tissue optics is the Henyey-Greenstein phase function with g being the average scattering angle $\langle \cos \Omega \cdot \Omega' \rangle$:

$$p(\Omega \cdot \Omega') = \frac{1 - g^2}{4\pi(1 + g^2 - 2g\Omega \cdot \Omega')^{3/2}}. \quad (3)$$

Partial reflection of light at the tissue-air interface can be caused by the refractive index mismatch between animal tissue, $n_m$, and air, $n_0$, and the fraction of reflected light is given by the reflectivity $R(\Omega \cdot n, \lambda)$. The reflectivity can be a function of wavelength and direction of light propagation. Hence, the partly-reflecting boundary condition, with n being the outer surface normal of the boundary, can be given by, e.g.:

$$\psi(r, \Omega, \lambda) = R(\Omega' \cdot n, \lambda) \psi(r, \Omega', \lambda) \text{ with } \Omega' \cdot n < 0. \quad (4)$$

The exemplary detector readings at the tissue boundary can be obtained from the exiting partial current or photon boundary flux, $J^+(r, \lambda)$, in units of photons $s^{-1} cm^{-2}$, e.g.:

$$J^+(r, \lambda) = \int_{\Omega \cdot n > 0} [1 - R(\Omega \cdot n, \lambda)](\Omega \cdot n) \psi(r, \Omega, \lambda) d\Omega. \quad (5)$$

For solving the ERT for media with general geometries and non-uniform optical tissue parameter distributions, high-order approximations to the ERT can be used that are more easily solved for such complex problems. These approximations can include the discrete ordinate ($S_N$) method, the spherical harmonics ($P_N$) method, and the simplified spherical harmonics ($SP_N$) procedure. ERT-approximations can transform the integro-differential equation into algebraic systems of coupled differential equations. For example, N(N+2) coupled equations can be obtained for the $S_N$ method, $(N+1)^2$ equations can be obtained for the $P_N$ procedure, and $(N+1)/2$ equations can be obtained for the $SP_N$ equations. The $SP_N$ procedure with N=3 can be a suitable candidate in terms of accuracy and computational effort for solving the forward problem in luminescence tomography.

A1(a) Exemplary $SP_3$ Equations

An exemplary solution of exemplary $SP_3$ equations can provide the partial current of light, $J^+$, on the tissue surface for given light sources, $Q_m$, and optical tissue properties, $\mu$. The $SP_3$ equations can be two coupled diffusion equations for the moments $\phi_1$ and $\phi_2$, e.g.:

$$-\nabla \cdot \frac{1}{3\mu_{a1}} \nabla \varphi_1 + \mu_a \varphi_1 = Q_m + \frac{2}{3} \mu_a \varphi_2 \quad (6a)$$

$$-\nabla \cdot \frac{1}{7\mu_{a3}} \nabla \varphi_2 + \left(\frac{4}{9}\mu_a + \frac{5}{9}\mu_{a2}\right) \varphi_2 = -\frac{2}{3} Q_m + \frac{2}{3} \mu_a \varphi_1 \quad (6b)$$

The boundary conditions can be given by, e.g.:

$$\left(\frac{1}{2} + A_1\right)\varphi_1 + \left(\frac{1 + B_1}{3\mu_{a1}}\right) n \cdot \nabla \varphi_1 = \left(\frac{1}{8} + C_1\right)\varphi_2 + \left(\frac{D_1}{\mu_{a3}}\right) n \cdot \nabla \varphi_2 \quad (7a)$$

$$\left(\frac{7}{24} + A_2\right)\varphi_2 + \left(\frac{1 + B_2}{7\mu_{a3}}\right) n \cdot \nabla \varphi_2 = \left(\frac{1}{8} + C_2\right)\varphi_1 + \left(\frac{D_2}{\mu_{a1}}\right) n \cdot \nabla \varphi_1 \quad (7b)$$

Then, the partial current can be obtained from solutions, $\phi_1$ and $\phi_2$, e.g.:

$$J^+ = \left(\frac{1}{4} + J_0\right)\left(\varphi_1 - \frac{2}{3}\varphi_2\right) - \left(\frac{0.5 + J_1}{3\mu_{a1}}\right) n \cdot \nabla \varphi_1 + \left(\frac{5}{16} + J_2\right)\left(\frac{1}{3}\varphi_2\right) - \left(\frac{J_3}{7\mu_{a3}}\right) n \cdot \nabla \varphi_2 \quad (8)$$

The $SP_3$ equations can overcome the limits of low-order approximations, i.e., the diffusion equation, when large light absorption and small geometries are present. For example, previous studies have shown that diffusion solutions deviate from $S_N$-transport solutions by over 50% at absorption coefficients larger than 2 $cm^{-1}$, whereas $SP_3$ solutions can show a model error of less than 3%. Moreover, solving the $SP_3$ equations can be significantly less time-consuming than solving the ERT with $S_N$ or $P_N$ equations. For example, previous studies have shown that solutions to the $SP_3$ equations can be found at least 100 times faster than solutions to a $S_{16}$ method. Further, $SP_3$ solutions can be obtained only at a factor of 2.5 slower than finding a diffusion solution.

A1(b) Exemplary Blocking-Off FD Method with Regular Grids

The exemplary $SP_3$ equations can be solved with an exemplary FD procedure on regular grids containing M equidistant grid points. The exemplary blocking-off FD procedure can use a structured grid for modeling the curved or irregular geometries of the small animal. Structured grid calculations can take less time than unstructured grid calculations because numerical solvers for structured grids, such as multigrid techniques, can be more efficient. Moreover, data storage and accessibility of neighboring grid points of regular or structured grids can be faster than for irregular or unstructured grids. Neighboring grid points of regular grids can be simply found by adding or subtracting "1" from grid point indices in a 3D data array. Irregular grids, on the other hand, can require storage of cell-to-cell pointers in a one-dimensional (1D) data array, which can provide a list of the connectivity between neighboring cells, leading to more storage and slower code execution.

The physical domain of the animal can be represented by a so-called nominal domain that can be divided into two regions. First, the active region can be part of the physical domain where the solution of the $SP_3$ equations is sought. Second, the inactive region can lie outside the physical boundary. The active region can be generated by identifying all grid points that are enclosed by the physical boundary. Hence, the tissue boundary can be approximated by grid points of the active region closest to the physical tissue boundary. The $SP_3$ equations (e.g., 6a, 6b) can be solved on the interior grid points of the active region, whereas the boundary equations (e.g., 7a, 7b) can be solved on the boundary grid points of the active region approximating the curved geometry of the small animal.

Figure 2:
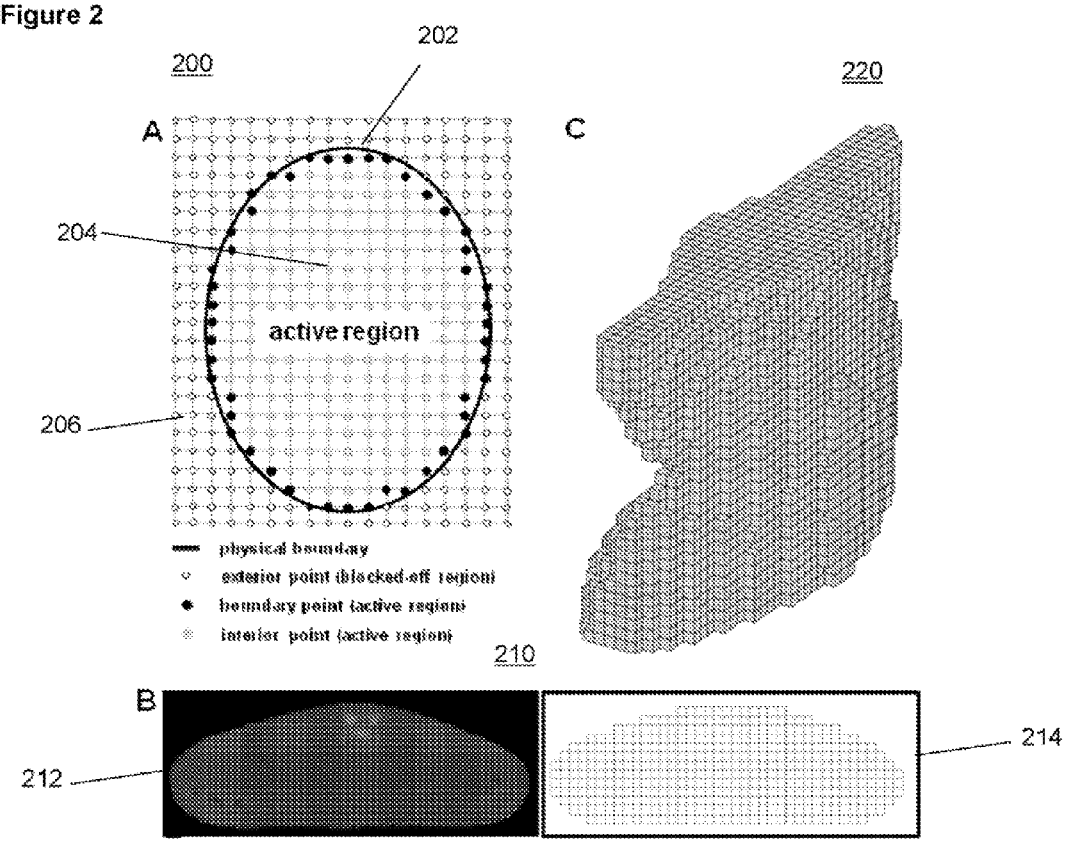
FIG. 2A is an illustration of an exemplary structured grid according to certain exemplary embodiments of the present disclosure.
FIG. 2B are illustrations of an exemplary CT image and an exemplary structured grid according to certain exemplary embodiments of the present disclosure.
FIG. 2C is an illustration of an exemplary structured small animal according to certain exemplary embodiments of the present disclosure.

FIG. 2 shows an illustration of both regions defined around the physical boundary. For example, FIG. 2A shows an exemplary structured grid 200 with a physical boundary 202 separating an active region 204 and a blocked-off region 206. FIG. 2B shows an exemplary CT image 210 representing the physical domain boundary (left—212) and an exemplary structured grid representing the computational domain (right—214). FIG. 2C shows an exemplary three-dimensional (3D) structure 220 of a small animal (e.g., dorsal side to the left, ventral side to the right). The blocked-off region procedure can be used to sustain high numerical accuracy if the grid size is sufficiently fine. For example, a maximum displacement of a detector point on the physical boundary can be less than 0.025 cm on the regular grid when using a grid size with 0.05 cm grid point separation. Thus, the error due to displacement can be within the experimental error of determining the physical boundaries of a scattering medium.

A2 Exemplary Inverse Model

The exemplary inverse model, $F^{-1}$, can describe and/or facilitate a functional relationship $Q=F^{-1}(J^+)$ between the unknown luminescent source distribution, Q, and the given boundary measurements, $J^+$. This inverse problem can be largely underdetermined because there can be fewer boundary data available than sought source points inside the tissue. Therefore, exemplary spectral procedures can be provided that utilize the spectral dependence of the absorption and scattering coefficients of tissue to increase the amount of independent boundary data. Large changes of light absorption, for example, over three orders of magnitude can be observed within the spectral range of about 550 nm and 700 nm primarily due to the (oxy-) hemoglobin content of biological tissue. This spectral range can overlap with the emission spectrum of a luciferase/luciferin reporter system and the emission spectrum of Cerenkov light. Accordingly, the luminescence light distribution on the tissue surface can be wavelength-dependent and can be used for solving the inverse source problem in luminescence tomography.

Based on the spectral dependence of $\mu_s$ and $\mu_a$ and the functional relationship between $J^+$ and $\mu_s$ and $\mu_a$, prior knowledge of the optical parameters can be helpful for solving the inverse source problem. Inaccurate optical parameters can substantially distort the luminescent source solution and, therefore, $\mu_s$ and $\mu_a$ are preferably either determined from ex vivo or from in vivo measurements. A beneficial feature of certain exemplary procedure described herein can be that the average absorption and scattering coefficients can be computed at each wavelength prior to reconstructing the reporter probe distribution. Accordingly, model errors can be substantially reduced during the source reconstruction, which may originate from inaccurate absorption and scattering coefficients.

The exemplary luminescence source image reconstruction can be broken up into two steps and/or procedures. First, the inverse optical parameter problems $\mu_a = F^{-1}(Q,J^+,\mu_s)$ and $\mu_s = F^{-1}(Q,J^+,\mu_a)$ can be solved for obtaining the unknown absorption and scattering coefficients for a well-known source distribution Q and boundary current $J^+$ at each wavelength. It can be assumed for simplicity that the tissue can be optically uniform and, hence, can fully be described, e.g., by a single absorption and a single scattering coefficient for a given wavelength range. Second, the inverse source problem $Q=F^{-1}(J^+,\mu_s,\mu_a)$ can be solved for a given partial boundary current originating from luminescent sources Q.

A2(a) Exemplary Reconstruction of Absorption and Scattering Coefficients

An exemplary evolution strategy and/or procedure (ES) with self-adaptation can be implemented for calculating the average absorption and scattering coefficients, $\mu_a$ and $\mu_s$, as a function of wavelength. By using an optically uniform tissue model, the inverse optical parameter problem can be simplified by reducing the total number of unknowns. The uniform tissue model can also be expanded into a non-uniform model by assigning different optical parameters to segmented tissue parts based on MR images as described above.

The exemplary calculation of $\mu_a$ and $\mu_s$ for $\Lambda$ selected wavelengths of the luminescence spectrum can involve: (i) a known source location with known spectrum preferably similar to the luminescent reporter probe spectrum, and (ii) measurements, Y, of the partial boundary flux for $\Lambda$ wavelengths. The exemplary wavelength-dependent partial boundary flux can become input to the ES, whereas the known source location can be used for calculating a predicted partial boundary flux $J^+$. The known source location can be given, for example, by a laser diode or a white light source with a bandpass filter of defined wavelength that can be placed on top of the tissue surface.

An exemplary ES with self-adaptation can approximately or substantially mimic the evolution process in nature by randomly modifying a population of member variables throughout generations and selecting the fittest population member in each generation cycle. It can be an exemplary iterative procedure that can minimize an error function $\phi$ by probing the global search space of the unknown spectrally-dependent absorption and scattering coefficients. The error function can be a weighted $X^2$-error norm of the measured ratios, RY, and predicted ratios, $RJ^+$, of partial current for $\Lambda$ selected wavelengths of the given source, e.g.:

$$\phi(\mu_a, \mu_s) = \sum_r^R \frac{1}{N} \sum_{n=1}^N \frac{(RY_{r,n} - RJ^+_{r,n})^2}{\sigma^2_{r,n}}. \tag{9}$$

The maximum number, R, of ratios can be given with, e.g.:

$$R = \sum_{n=1}^{\Lambda-1} n.$$

For example, for $\Lambda=4$ wavelengths, a maximum of R=6 ratios can be obtained. These ratios, $RY_{r,n}$ and $RJ^+_{r,n}$, can be given by:

$$RY_{r=1,n} = \frac{Y_{1,n}^{\lambda=1}}{Y_{1,n}^{\lambda=2}},$$

$$RY_{r=2,n} = \frac{Y_{2,n}^{\lambda=1}}{Y_{2,n}^{\lambda=3}},$$

$$RY_{r=3,n} = \frac{Y_{3,n}^{\lambda=1}}{Y_{3,n}^{\lambda=4}},$$

$$RY_{r=4,n} = \frac{Y_{4,n}^{\lambda=2}}{Y_{4,n}^{\lambda=3}},$$

$$RY_{r=5,n} = \frac{Y_{5,n}^{\lambda=2}}{Y_{5,n}^{\lambda=4}},$$

$$RY_{r=6,n} = \frac{Y_{6,n}^{\lambda=3}}{Y_{6,n}^{\lambda=4}}$$

and $$RJ_{r=1,n} = \frac{J_{1,n}^{\lambda=1}}{J_{1,n}^{\lambda=2}},$$

$$RJ_{r=2,n} = \frac{J_{2,n}^{\lambda=1}}{J_{2,n}^{\lambda=3}},$$

$$RJ_{r=3,n} = \frac{J_{3,n}^{\lambda=1}}{J_{3,n}^{\lambda=4}},$$

$$RJ_{r=4,n} = \frac{J_{4,n}^{\lambda=2}}{J_{4,n}^{\lambda=3}},$$

$$RJ_{r=5,n} = \frac{J_{5,n}^{\lambda=2}}{J_{5,n}^{\lambda=4}},$$

$$RJ_{r=6,n} = \frac{J_{6,n}^{\lambda=3}}{J_{6,n}^{\lambda=4}}.$$

The quantity $\sigma_{r,n}$ can constitute the confidence in the measurements given represented by the noise level of the detector. For example, $\sigma_{r,n}$ can be estimated by the ratio $RY_{r,n}$. The total number of exemplary measurement data, $N=\Lambda D$, can be given for the partial current at all D detector point positions at the tissue surface and for $\Lambda$ wavelengths of the bioluminescence spectrum.

An exemplary ES can involve a parent population with P members and an offspring population with O>P members. Each population member can be a data vector involving $2\Lambda$ object variables of $\mu_{a,s}(\lambda)$ and $2\Lambda$ strategy parameters $\sigma_{a,s}(\lambda)$. The members of the parent population can be inherited to the offspring population by mutual recombination of data vectors of individual parent members $\mu_{a,s}^A$ and $\mu_{a,s}^B$, e.g.:

$$\mu_{a,s}(\lambda) = \frac{\mu_{a,s}^A(\lambda) + \mu_{a,s}^B(\lambda)}{2}. \tag{10}$$

Each member $\mu_{a,s}(\lambda)$ of the offspring population can be randomly altered now by mutation, e.g.:

$$\mu_{a,s}^{new}(\lambda) = \mu_{a,s}(\lambda) + N(0, \sigma_{a,s}(\lambda)). \tag{11}$$

The exemplary strategy parameter $\sigma_{a,s}(\lambda)$ can define the standard deviation of a Gaussian normal distribution N. Self-adaptation of the exemplary ES can be obtained when the strategy parameter $\sigma_{a,s}(\lambda)$ is subject to recombination and mutation as well. Here, $\sigma_{a,s}$ can be modified at each generation cycle by the mutation, e.g.:

$$\sigma^{new}(\lambda) = \sigma(\lambda) e^{\tau N(0,1)} \tag{12}$$

and can be controlled by the self-adaptation parameter $\tau$. For example, the fittest offspring, having the smallest error function, can be selected and become the new parent population of the next generation cycle. This exemplary process can be repeated until convergence of $\phi$, when the ratios of the partial currents $J^+$ match the ratios of the measured partial currents Y. This exemplary optimization process can be relatively fast in comparison to the luminescent source reconstruction of M unknown source points because only $2\Lambda$ unknown absorption and scattering coefficients are found. The recovered absorption and scattering coefficients can become input to the inverse source problem solver, which will be described herein below.

A2(b) Exemplary Reconstruction of Source Distribution

An exemplary unknown luminescent source distribution can be reconstructed from the given spectrally dependent partial boundary currents Y and previously calculated absorption and scattering parameters $\mu_{a,s}(\lambda)$. The partial current $J^+$ in equation (2) can be replaced by its noise-corrupted counterpart Y, i.e., experimental data, and an algebraic system of equations $Q=F^{-1}(\mu_{a,s}, Y)$ can be built by casting Q and Y into vectors and $F(\mu_{a,s})$ into a matrix, e.g.:

$$Y = FQ. \tag{13}$$

The exemplary vector Y can have $N=\Lambda D$ elements $Y_n$, the exemplary vector Q can have M elements $Q_m$, and the exemplary matrix F can have of $M \times N$ elements $F_{nm}$. Each exemplary matrix element $F_{nm}$, given by the partial boundary current $J^+(\lambda)$. $J^+(\lambda)$ at detector point $r_d$, can be computed by solving the exemplary $SP_3$ equations for a given unit source $Q_m$ defined at grid point $r_m$ and absorption and scattering coefficient $\mu_{a,s}$ of wavelength $\lambda$. Moreover, when using a non-uniform tissue map obtained from exemplary segmented MR images, $J^+$ can be calculated for a non-uniform distribution of $\mu_{a,s}$. Here, the non-uniform tissue model can involve a bulk tissue domain, which can be described by the pre-calculated $\mu_a(\lambda)$, and of a segmented tissue domain with modified optical parameters.

The exemplary numerical build-up of the matrix F can be time-consuming because the exemplary $SP_3$ equations would be solved for each source $Q_m$ of all M interior grid points. However, the build-up of F can be sped up, for example, by using the reciprocity theorem. Here, the exemplary matrix elements $F_{nm}$ can be determined by solving the $SP_3$ equations for placing an exemplary virtual source $Q_d$ at each detector point position at the tissue boundary. The exemplary photon flux obtained at interior grid point $r_m$ can be assigned to $F_{nm}$. Since D<M, an approximate speed-up factor of M/D can be obtained.

The system of equations (13) can then be solved for the exemplary unknown vector Q with an exemplary expectation-maximization (EM) procedure or any other applicable solver for linear algebraic systems of equations.

A3 Exemplary MRI/CT Co-Registration

Exemplary MRI co-registration can serve many functions. For example, segmented MR images can be used for defining non-uniform optical tissue property maps when, e.g., large deviations of $\mu_a$ or $\mu_s$ from the average properties, as can be determined by the ES or the empirical scattering function (11), are present. In addition, MR images can also be used for co-locating the reconstructed luminescent source distributions to anatomical tissue structures. The exemplary CT co-registration can be utilized when defining the surface geometry of the animal and/or for validation studies.

Exemplary registration procedures can be based on a calibrated positioning of the animal within each scanner's field of view. Between and during the imaging sessions, the animal can be held in a rigid pose, e.g., at a fixed position relative to the animal bed. Exemplary Registration can be performed by establishing a frame of reference relative to the bed for each scanner and calculating the rigid or projective transforms that map between them.

The exemplary absorption and scattering coefficients of different tissue types can be assigned to the segmented tissues from the MR or CT images. The exemplary absorption and scattering coefficients can be determined from an empirical scattering function and the extinction spectrum and concentration of (oxy-)hemoglobin in different organs prior to image reconstruction. The exemplary reduced scattering coefficient can satisfy a power law relationship [14,15], e.g.:

$$\mu_s' = 1/(1-g)a\lambda^{-b} \tag{14}$$

The exemplary spectrally dependent parameters a and b can be given, for example, in exemplary equation [10].

The exemplary spectrally dependent absorption coefficients can be given with, e.g.:

$$\mu_a(\lambda) = S_B[x\mu_{aHb}(\lambda) + (1-x)\mu_{aHbO_2}(\lambda)] + S_W \mu_{aW}(\lambda)[\text{cm}^{-1}] \tag{15}$$

$$x = \frac{HbO_2}{(HbO_2 + Hb)}$$

Figure 3:
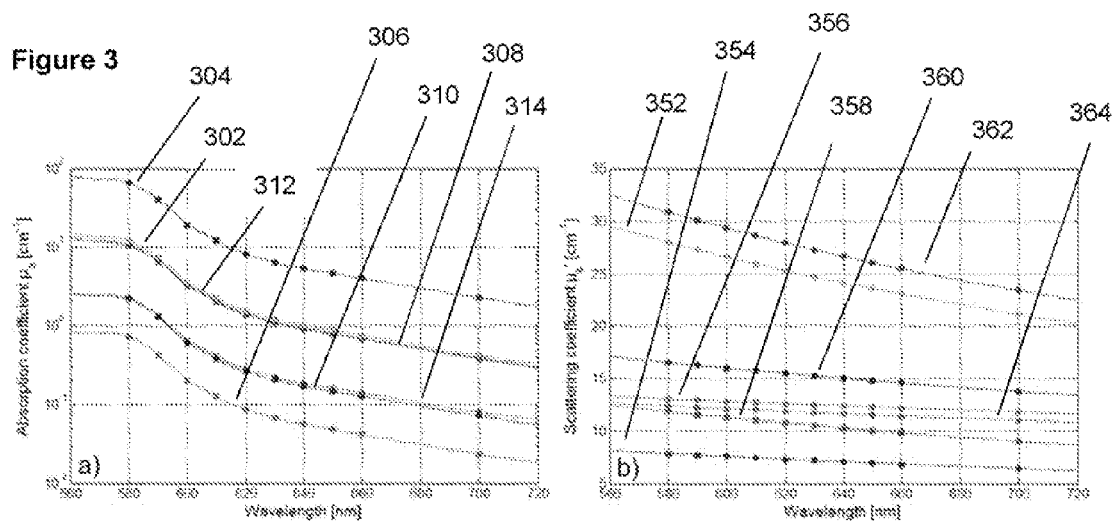
FIGS. 3A and 3B are graphs of exemplary plots of optical parameters for various organs according to certain exemplary embodiments of the present disclosure.
Figure 4:
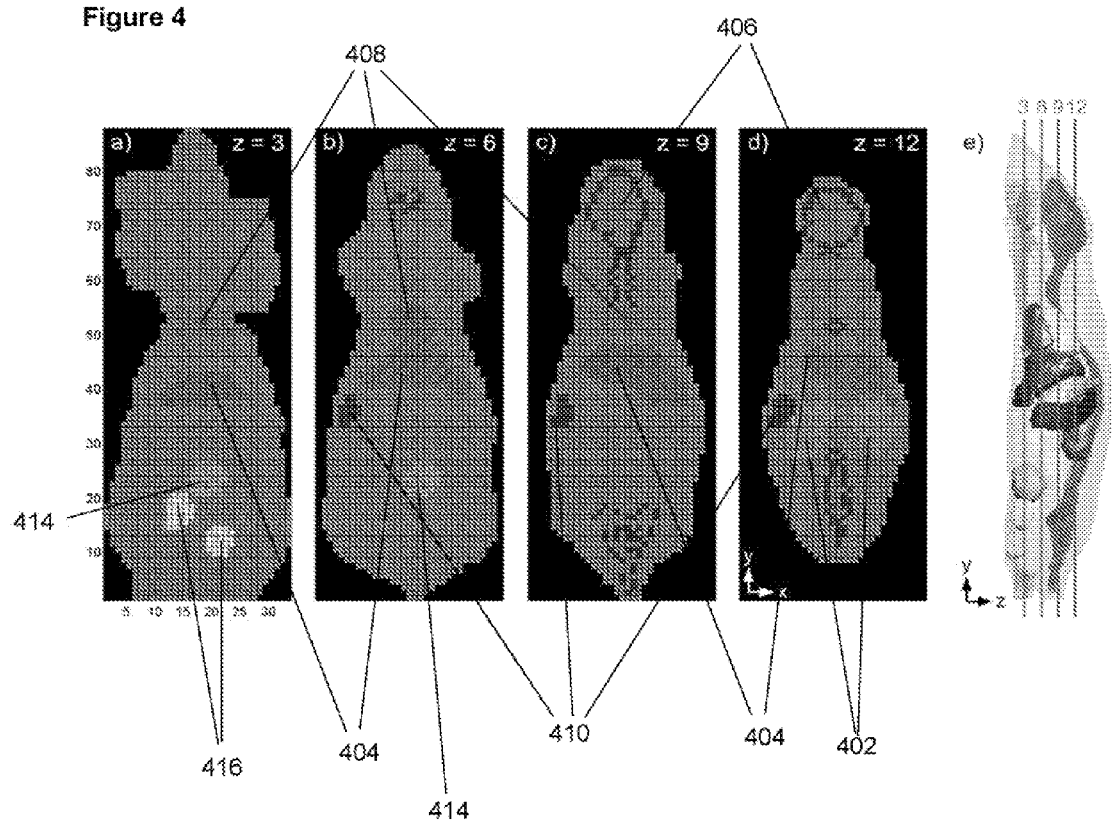
FIGS. 4A-4E are exemplary images of a mouse model with various organ and optical parameters according to certain exemplary embodiments of the present disclosure.

$\lambda$: wavelength $\mu_s'(\lambda)$: reduced scattering coefficient $\mu_a(\lambda)$: absorption coefficient $\mu_{aHbO_2}(\lambda)$: absorption *coeff.* oxy-hemoglobin $\mu_{aHb}(\lambda)$: absorption *coeff.* deoxy-hemoglobin $\mu_{aW}(\lambda)$: absorption *coeff.* water a, b: empirical constants $S_B, S_W$: scaling factors FIGS. 3A and 3B illustrate exemplary plots of both optical parameters for different organs which can be utilized with the exemplary embodiments of the system, method and computer-accessible medium according to the present disclosure. FIG. 3A shows a graph of exemplary absorption coefficients of a kidney (302), liver (304), brain (306), heart (308), stomach (310), bone (312), bladder (314), and testicles (316). FIG. 2B shows a graph of exemplary scattering coefficients of a kidney (352), liver (354), brain (356), heart (358), stomach (360), bone (362), bladder (364), and testicles (366). FIGS. 4A-4D illustrate images of exemplary 3D mouse models with different organs and optical parameters which can also be utilized with the exemplary embodiments of the system, method and computer-accessible medium according to the present disclosure. For example, the kidney (402), liver (404), brain (406), heart (408), stomach (410), bone (412), bladder (414), and testicles (416) are shown in the images of FIGS. 4A-4D.

B. Exemplary Demonstration

Exemplary experiments/demonstrations/implementations/utilization of certain exemplary embodiments of the present disclosure can include in vivo experiments that show, e.g., that multispectral attenuation-corrected luminescence tomography with explicit calculation of uniform tissue attenuation (e.g., absorption coefficients and scattering coefficients) maps can significantly improve image quality. Further, exemplary MRI/CT co-registration can provide, e.g., non-uniform tissue attenuation maps and, furthermore, relative anatomical co-location of the exemplary reconstructed luminescent reporter probe distribution.

The exemplary ES was tested for recovering the wavelength-dependent absorption and scattering coefficients under, e.g., conditions by using a numerical mouse model. Then, the average absorption coefficient of a small animal was reconstructed by using an artificial implanted light source and the exemplary validated ES. Animal experiments were conducted and the Cerenkov light source distribution was recovered of a nuclear reporter system with a known location. The results were co-registered to exemplary PET images. A bioluminescent source reporter system was reconstructed in a small animal. The results were then co-registered to exemplary anatomical MR images.

B1 Exemplary Calculation of Attenuation Maps (Absorption and Scattering Coefficients) with an Evolution Strategy B1(a) Numerical Simulations The accuracy of an exemplary ES for recovering the absorption coefficients of a numerical mouse model, for example, was tested. The exemplary mouse model was defined, for example, on a structured grid with 32,256 grid points. The surface geometry of the exemplary mouse model was derived from CT images. The CT scanner was, for example, a Siemens/CTI microCAT II (Siemens Medical Solutions, Malvern, Pa.) with an 8.5 cm axial by 5.0 cm transaxial field-of-view. The CT scanner used a 2048×3096 element CCD array coupled to a high-resolution phosphor screen via a fiber-optic taper. The Tungsten anode had a focal spot of 6 microns. The highest reconstructed resolution obtained with the small animal CT scanner is about 15 microns in each dimension.

Uniform optical properties were assigned, for example, at six different wavelengths to each grid point and modeled a point source in the center of the bowel area of the animal. For example, the reduced scattering coefficient was 12 cm$^{-1}$, whereas the absorption coefficient was 0.05, 0.1, 0.15, 0.25, 0.8, and 2 cm$^{-1}$ with descending order in wavelength (660 nm to 560 nm in 20 nm steps). Next, synthetic measurement data, Y, was calculated for all six wavelengths and 190 detector points at the dorsal side of the animal. The exemplary synthetic measurement data became input to the exemplary ES and the assumingly unknown absorption coefficients were calculated. The exemplary ES used 500 parent members, 3500 offspring, and a self-adaptation parameter $\tau$=0.4. The exemplary ES optimization was terminated after 25 generations. The total reconstruction time took approximately 15 seconds on a 3 GHz Intel processor. The exemplary recovered absorption coefficients were calculated to be, for example, about 0.055 cm$^{-1}$ (660 nm), 0.101 cm$^{-1}$ (640 nm), 0.152 cm$^{-1}$ (620 nm), 0.255 cm$^{-1}$ (600 nm), 0.812 cm$^{-1}$ (580 nm), and 2.017 cm$^{-1}$ (560 nm). 10 additional numerical experiments were performed by varying the absorption coefficients at all wavelengths and determined the relative error of the recovered from the original absorption coefficient. It was found that the exemplary ES can determine the absorption coefficient at all six wavelengths within an average error of approximately 14.2%.

B1(b) Exemplary in Vivo Test

Exemplary average absorption coefficients of a small animal were determined utilizing certain exemplary embodiments of the present disclosure by using exemplary in vivo measurement data of the boundary flux at six different wavelengths between 560 nm and 660 nm. The known source, which can be used for the inversion process, was a gaseous tritium-powered light source (GTLS) that can be placed within the animal using a rectal catheter. The GTLS can mimic the luminescence spectrum of a luciferase-luciferin reporter system. The same can be performed for a Cerenkov light spectrum. The spatial location of the light source within the animal was determined from co-registered CT images. A regular grid was generated with 32,256 grid points and identified the surface geometry from the co-registered CT images. Luminescence images were taken from the animal's dorsal side at six wavelengths ranging from about 560 nm to 660 nm with a filter separation of 20 nm. A luminescence imaging system (IVIS 200, Caliper Sciences, USA) was used that was equipped with wavelength selecting filters having a bandwidth of 20 nm.

The exemplary average absorption coefficients were determined as a function of wavelength of the assumed optically uniform tissue distribution by solving the functional relation $\mu_a = F^{-1}(Q, Y, \mu_s')$ for the given GTLS and measured partial currents. The exemplary measured partial currents and source location became input to the ES. The exemplary reconstructed absorption coefficients are shown in Table 1. Table 1 indicates, for example, exemplary average absorption coefficients [cm$^{-1}$] of a uniform tissue model calculated by the evolution strategy given in vivo GTLS bead light intensity data and exemplary absorption coefficients [cm$^{-1}$] of different small animal tissues calculated by an empirical function based on the oxygenation level (see, e.g., exemplary equation 15). In comparison to the exemplary absorption coefficients of different tissue types shown in Table 1, the exemplary reconstructed absorption coefficients are closest, for example, to the coefficients of bowl tissue.

TABLE 1

|  | 560 nm | 580 nm | 600 nm | 620 nm | 640 nm | 660 nm |
|---|---|---|---|---|---|---|
| 1. Reconstructed with Evolution strategy | 2.21 | 2.23 | 0.71 | 0.21 | 0.08 | 0.04 |
| 2. Bowel | 2.49 | 1.99 | 0.62 | 0.27 | 0.18 | 0.13 |
| 3. Muscle | 18.73 | 14.98 | 4.68 | 2.04 | 1.35 | 1.0 |
| 4. Adipose | 0.84 | 0.73 | 0.20 | 0.09 | 0.06 | 0.04 |
| 5. Lung | 8.51 | 6.45 | 2.47 | 0.86 | 0.61 | 0.43 |
| 6. Kidneys | 3.17 | 2.74 | 1.05 | 0.45 | 0.32 | 0.21 |

Figure 5:
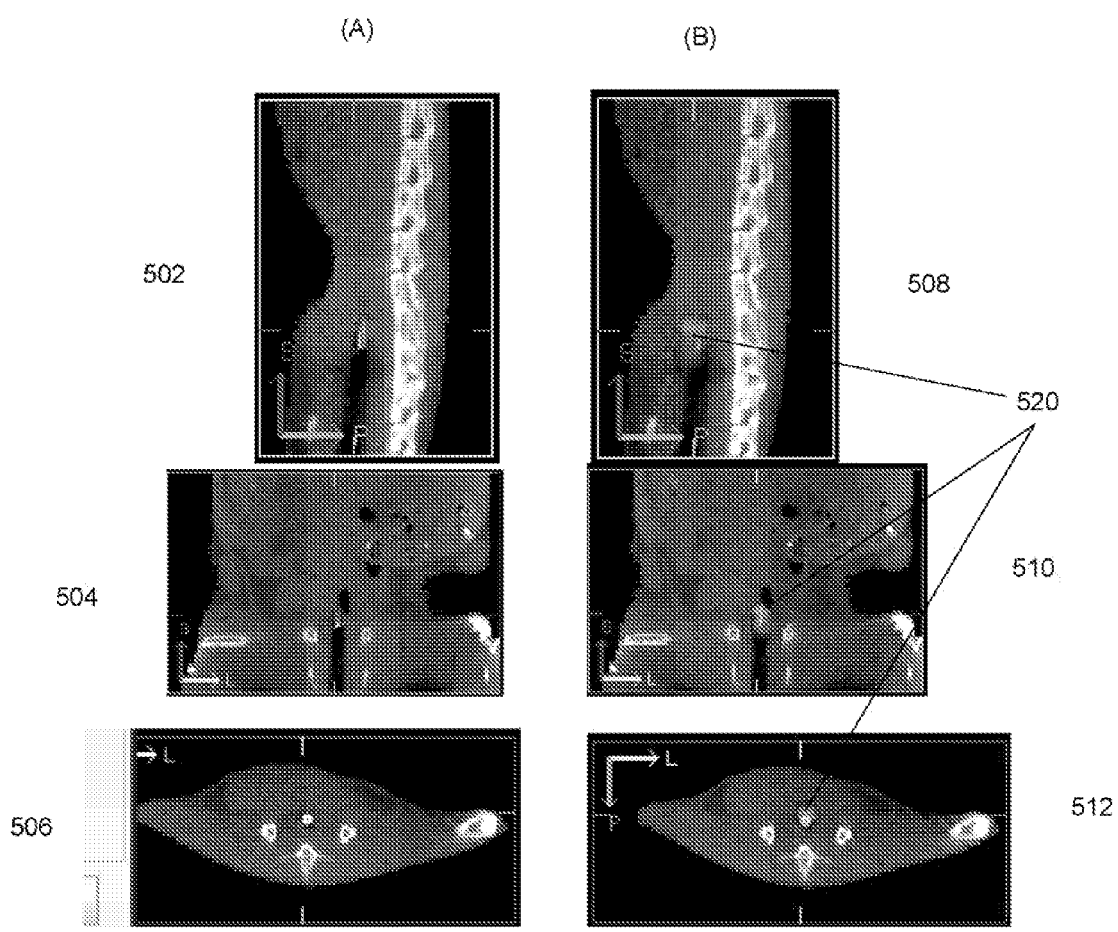
FIGS. 5A and 5B are exemplary CT images and exemplary reconstructed luminescence image according to certain exemplary embodiments of the present disclosure.

B2 Exemplary Multispectral Attenuation-Corrected Luminescence Tomography of GTLS Cylinders After determining the absorption and scattering coefficients with the exemplary ES, the previously known spatial position of the GTLS bead was reconstructed by solving the inverse source problem $Q = F^{-1}(Y, \mu_a, \mu_s')$. Such experiment can facilitate an estimation of the reconstruction performance of the exemplary source reconstruction technique in terms of accurate recovery of the spatial source location. The exemplary SP$_3$ equations and the source reconstruction was performed on the structured grid with M=32,256 grid points. The exemplary luminescence images taken with the CCD camera were assigned to D=190 detector points on the animal surface. Using Λ=6 wavelengths, a total of N=1140 boundary measurement points were obtained. The matrix F was built by solving the exemplary SP$_3$ equations in conjunction with the reciprocity approach. Based on the results, a speed-up factor of approximately M/D=170 could be obtained. The exemplary system was then solved with the exemplary EM method. The image reconstruction time took approximately 15 minutes and 48 seconds on a 3 GHz Intel processor. FIG. 5 illustrates exemplary images of the exemplary reconstructed source distribution over-layed on top of an exemplary CT image showing a GTLS bead 420. FIG. 5A shows sagittal (502), coronal (504), and transaxial (506) views of CT images, and FIG. 5B shows sagittal (508), coronal (510), and transaxial (512) views of luminescence image reconstruction images. As shown, the spatial location of the reconstructed source matches the location shown in the CT image.

B3 Multispectral Attenuation-Corrected Cerenkov Luminescence Tomography

Figure 6:
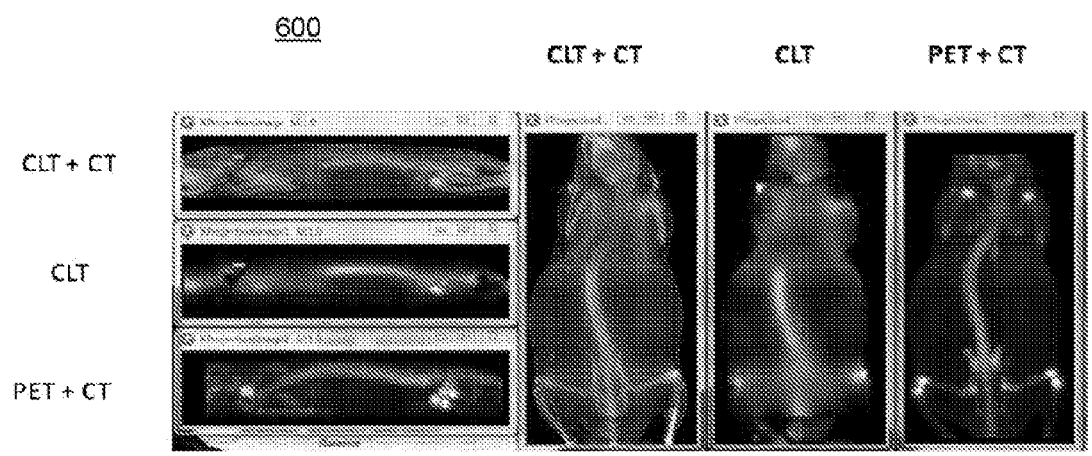
FIG. 6 is a set of exemplary luminescence tomography, CT scan and PET scan images according to certain exemplary embodiments of the present disclosure.

According to further exemplary embodiments of the present disclosure, the method, system and computer-accessible medium can be provided to test the exemplary procedures using a small animal that can display a significant nuclear reporter probe uptake in the skeleton. For example, this reporter probe can emit Cerenkov light. The Cerenkov light source distribution can be reconstructed, for example, on a 48×22×30 structured grid. The absorption and scattering coefficients reconstructed with the ES for a uniform mouse model can be used. The exemplary image reconstruction can employ dorsal and ventral views of the animal. The Cerenkov light images can be taken at four exemplary wavelengths (e.g., 640 nm, 620 nm, 600 nm, 580 nm). The absorption coefficients can be, for example, 0.09, 0.21, 0.71, and 2.23 cm$^{-1}$, respectively, for the exemplary wavelengths. Each image can include approximately 520 image pixels (detector points), totaling 2080 detector points. The exemplary EM method can take, for example, about 500 iterations for completing the reconstruction. The exemplary resulting images are shown in FIG. 6. The Cerenkov luminescence tomography (CLT) images can be compared to PET images. For example, FIG. 6 shows exemplary images 600, which include Cerenkov luminescence tomography (CLT), CT scan, and positron emission tomography (PET) images of a whole body small animal scan. Further, nuclear reporter probe uptake is present in animal skeleton and clearly visible in the exemplary PET images, and the exemplary CLT images match the exemplary PET images.

B4 Multispectral Attenuation-Corrected Bioluminescence Tomography

Figure 7:
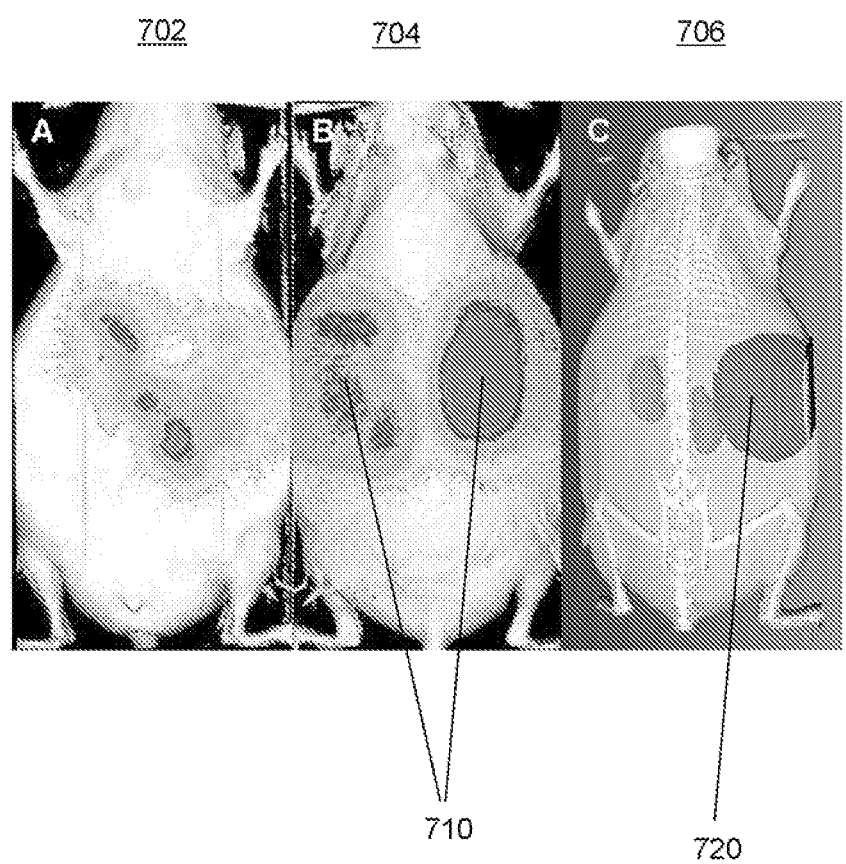
FIGS. 7A-7C are exemplary bioluminescence images according to certain exemplary embodiments of the present disclosure.

A performance of certain exemplary embodiments of the method for reconstructing a luciferase reporter system which is supported by MR-based image segmentation was shown in an experiment in which a transgenic mouse was used which was engineered such that its kidneys expressed click-beetle-red (CBR) luciferase. Exemplary bioluminescence images were acquired from both dorsal (as shown in an exemplary image of FIG. 7A) and ventral (as shown in an exemplary image of FIG. 7B) views at five different wavelengths of the bioluminescence spectrum (580 nm-660 nm; 20 nm separation). In particular, FIG. 7A shows an exemplary ventral image 602 and FIG. 7(B) shows an exemplary dorsal image 704 of measured bioluminescence light distribution on tissue surface. For example, light generally originates from luciferase-expressing cells located in both kidneys 710. FIG. 7(C) shows an exemplary dorsal view 606 of a surface-rendered image of mouse skin, skeleton, kidneys, and cyst. Such exemplary images can be provided, for example, by CT and MR images using, e.g., computer arrangements associated therewith.

The exemplary measurement process, system and computer-accessible medium according to one exemplary embodiment of the present disclosure can utilize a total of about 20 minutes of camera integration time and can be corrected or adjusted for changes in luminescence over this time period by interpolating the short open (e.g., filterless) acquisitions flanking each of the bandpass measures. This bioluminescence data set was co-registered with anatomical information derived from subsequently acquired MR (Bruker Biospec) images taken of the animal while maintained in the same fixed pose. The Bruker Biospec 47/40 (Bruker Biospin Inc., Karlsruhe, Germany) is a 4.7 Tesla 40 cm horizontal bore small animal imaging spectrometer equipped for multinuclear imaging studies and spectroscopy.

Based on the exemplary MR images, a cyst 620 in the proximity of the kidneys was segmented (as shown in an image of FIG. 7C). The reduced scattering coefficients of bowel tissue (as shown in Table 1) and the absorption coefficients, which were determined, for example, by the exemplary ES, were assigned to the bulk tissue of the animal. It was assumed that the void-like cyst had optical parameters of $\mu_a=0.02$ cm$^{-1}$ and $\mu_s'=0.5$ cm$^{-1}$ for wavelengths (e.g., optical properties similar to that of water). The regular grid of the mouse model was constructed from surface-rendered MR images and had M=52,992 grid points. The exemplary bioluminescence surface images of the IVIS system were mapped onto D=234 grid points of the animal model, yielding N=1, 170 measurement data points for all five wavelengths.

Figure 8:
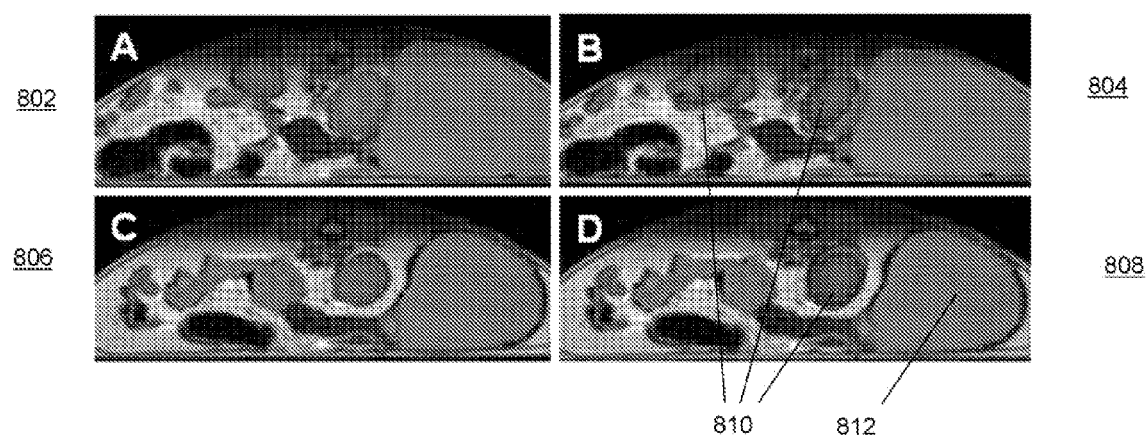
FIGS. 8A-8D are further exemplary MR and bioluminescence images according to certain exemplary embodiments of the present disclosure.

The exemplary image reconstruction procedure took approximately 23 minutes on a 3 GHz Intel processor. The 3D map of the bioluminescent reporter probe distribution was mapped onto the MR images (as shown in FIGS. 8A, 8C). FIGS. 8B and 8D illustrate two slices for different sections through the animal's torso. Both reconstructed kidneys are shown in FIG. 8B, whereas FIG. 8D shows one kidney in accordance with the exemplary MR image. In particular, FIGS. 8A and 8C show exemplary MR images 802 and 806 in gray-scale, and FIGS. 8B and 8D show exemplary superimposed bioluminescence image reconstructions 804 and 808, respectively, in hot-iron of luciferase-expressing kidneys. As illustrated in FIGS. 8A-8D, a cyst 812 is to the right, and correct location of both kidneys 810 is identified in bioluminescence image reconstructions.

Figure 9:
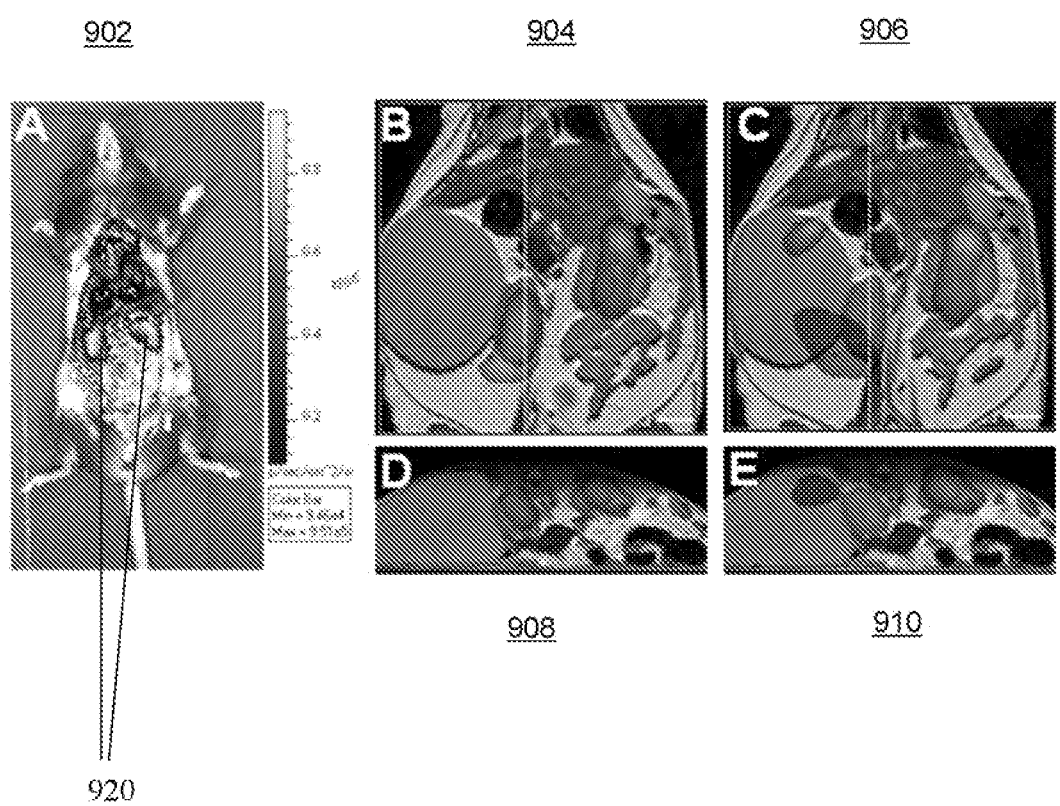
FIGS. 9A-9E are additional exemplary bioluminescence images according to certain exemplary embodiments of the present disclosure.

Moreover, the reconstructed reporter probe distribution is in accordance with bioluminescence images taken from the dissected animal (as shown in FIG. 9A). FIG. 9A shows an exemplary image 902 of a dissected transgenic mouse onto which the measured bioluminescence image in hot-iron has been superimposed. The abdomen of the animal has been opened surgically and some organs have been removed to provide a clear view of its click-beetle luciferase-expressing kidneys 920. The bioluminescence image has been taken immediately post-mortem and following a luciferin injection. FIGS. 9B-9E show various exemplary views of bioluminescence image reconstructions 904-910 of click-beetle reporter probe in kidneys prior to dissection. For example, FIGS. 9B and 9D show the correct location of both kidneys when including the non-uniform optical property maps of segmented cyst, obtained using the exemplary embodiments of the system, method and computer-accessible medium according to the present disclosure. Conversely, FIGS. 9C and 8E show false location of left kidney when optical property map of cyst is not included in BLT reconstruction and uniform optical property map is assumed.

It can be shown that both, the reconstructed (as shown in FIGS. 9B, 9D) and the dissected (as shown in FIG. 9A), images show the kidneys with a similar emission strength. For example, the dorsal and ventral views (as shown in FIGS. 7A, 7B) of the bioluminescence surface images do not show a similarly symmetric signal owing presumably to the differing depths of the two kidneys. The non-uniform optical property map of the animal with the low-scattering and low-absorbing cyst can have an impact on the accuracy of the exemplary bioluminescence image reconstruction. Despite the non-symmetric bioluminescence light distribution on the tissue surface, the exemplary BLT image reconstruction method is able to recover the correct position of the light-emitting kidneys with a similar source strength.

For comparison, the reporter probe distribution was also reconstructed without performing the cyst segmentation. The results are shown in FIGS. 9C and 9E. Here, the correct spatial location of both kidneys could not be recovered. It was concluded that the cyst with its significantly different optical parameters than the bulk tissue distorts the optical signal, and hence, the exemplary image reconstruction.

Figure 10:
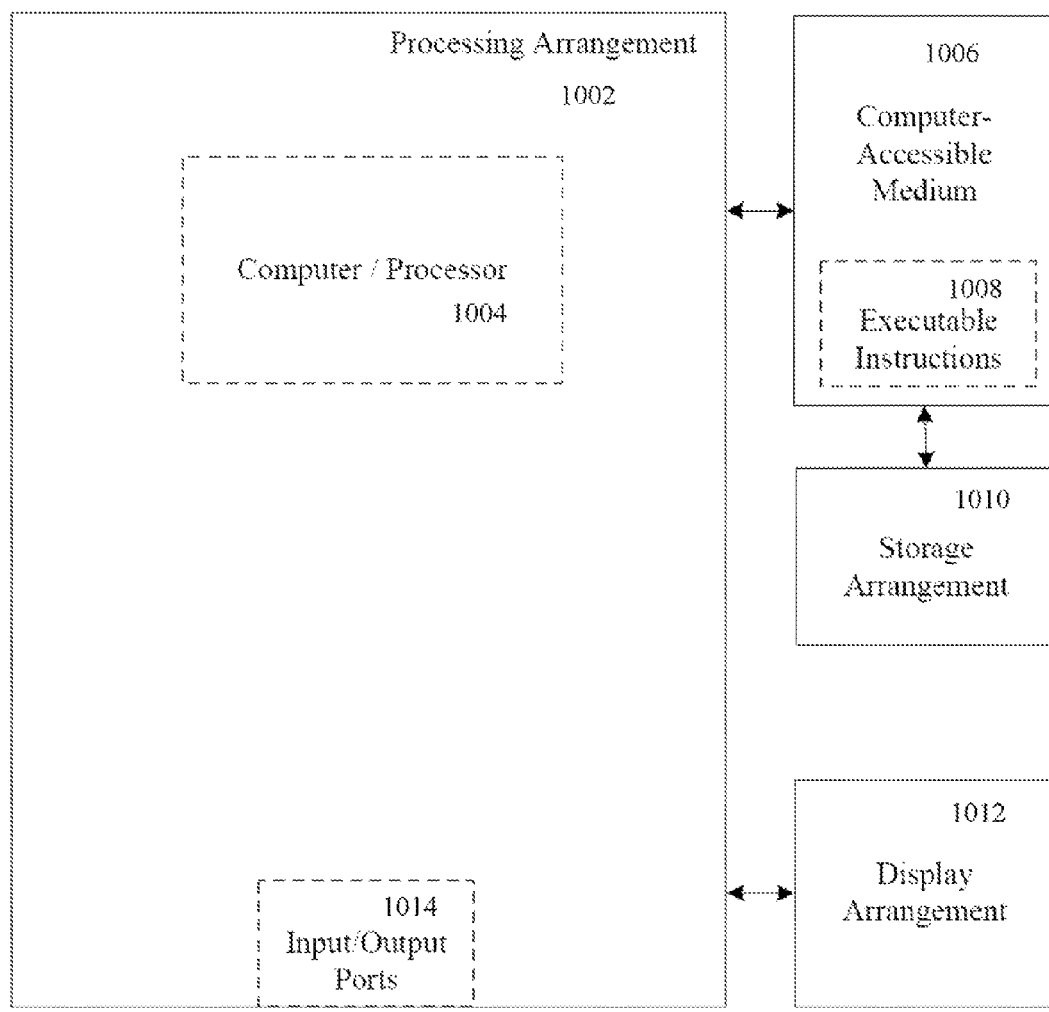
FIG. 10 is an illustration of an exemplary block diagram of an exemplary system in accordance with certain exemplary embodiments of the present disclosure.

FIG. 10 shows an exemplary block diagram of an exemplary embodiment of a system according to the present disclosure. For example, exemplary procedures in accordance with the present disclosure described herein can be performed by a processing arrangement and/or a computing arrangement 1002. Such processing/computing arrangement 1002 can be, e.g., entirely or a part of, or include, but not limited to, a computer/processor 1004 that can include, e.g., one or more microprocessors, and use instructions stored on a computer-accessible medium (e.g., RAM, ROM, hard drive, or other storage device).

As shown in FIG. 10, e.g., a computer-accessible medium 1006 (e.g., as described herein above, a storage device such as a hard disk, floppy disk, memory stick, CD-ROM, RAM, ROM, etc., or a collection thereof) can be provided (e.g., in communication with the processing arrangement 1002). The computer-accessible medium 1006 can contain executable instructions 1008 thereon. In addition or alternatively, a storage arrangement 1010 can be provided separately from the computer-accessible medium 1006, which can provide the instructions to the processing arrangement 1002 so as to configure the processing arrangement to execute certain exemplary procedures, processes and methods, as described herein above, for example.

Further, the exemplary processing arrangement 1002 can be provided with or include an input/output arrangement 1014, which can include, e.g., a wired network, a wireless network, the internet, an intranet, a data collection probe, a sensor, etc. As shown in FIG. 10, the exemplary processing arrangement 1002 can be in communication with an exemplary display arrangement 1012, which, according to certain exemplary embodiments of the present disclosure, can be a touch-screen configured for inputting information to the processing arrangement in addition to outputting information from the processing arrangement, for example. Further, the exemplary display 1012 and/or a storage arrangement 1010 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. For example, various exemplary embodiments described herein can be used interchangeably, in conjunction and together with other exemplary embodiments of the present disclosure. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications and references referred to herein are incorporated herein by reference in their entireties.

What is claimed is:

1. A method of generating particular information which is at least one of three-dimensional information or intensity information of a tissue portion which can include at least one of a tissue surface or a tissue volume, the method comprising:
    determining a light intensity distribution of light provided on the tissue portion;
    using the light intensity distribution, determining one or more attenuation maps of the tissue portion;
    obtaining one or more multispectral measurements of the light intensity distribution on the tissue portion taken from one or more views; and
    using a computer arrangement, generating the particular information using an image reconstruction procedure in conjunction with data from the one or more tissue attenuation maps and the multispectral measurements.

2. A non-transitory computer-accessible medium having instructions thereon for generating particular information which is at least one of three-dimensional information or intensity information of a tissue portion which can include at least one of a tissue surface or a tissue volume, wherein, when a computer arrangement executes the instructions, the computing arrangement is configured to:
    calculate a light intensity distribution of light provided on the tissue portion;
    use the light intensity distribution, determining one or more attenuation maps of the tissue portion;
    obtain one or more multispectral measurements of the light intensity distribution on the tissue volume taken from one or more views; and
    generate the particular information using an image reconstruction procedure in conjunction with data from the one or more tissue attenuation maps and the multispectral measurements.

3. The computer-accessible medium of claim 2, wherein the tissue volume comprises a curved tissue surface.

4. The computer-accessible medium of claim 3, wherein the light intensity distribution is calculated for a given set of point sources on the curved tissue surface.

5. The computer-accessible medium of claim 2, wherein the light intensity distribution is calculated using a light propagation model.

6. The computer-accessible medium of claim 5, wherein the light propagation model includes at least one of a radiative transfer procedure, a simplified harmonics procedure, or a diffusion procedure.

7. The computer-accessible medium of claim 6, wherein the simplified spherical harmonics procedure includes a diffusion equation that is solved with at least one of a finite-difference procedure, a finite volume procedure, or a finite element procedure.

8. The computer-accessible medium of claim 7, wherein the solving procedure includes using at least one of structured grids with equidistant grid points that define a domain of the tissue volume or unstructured grids with irregular grid point separations which define a domain of the tissue volume.

9. The computer-accessible medium of claim 2, wherein the one or more attenuation maps of the tissue volume are represented by absorption and scattering coefficients of the tissue.

10. The computer-accessible medium of claim 2, wherein the one or more attenuation maps of the tissue volume are determined by one or more of: (1) a light propagation model; (2) a global parameter optimization technique; and (3) a give source distribution.

11. The computer-accessible medium of claim 2, wherein the computing arrangement is further configured to reconstruct a source distribution by one or more of: (1) determining a light propagation model; (2) the one or more attenuation maps of the tissue volume; and (3) a linear image reconstruction procedure.

12. The computer-accessible medium of claim 2, wherein the information includes at least one a source power density, a source distribution in 3D space, or a concentration distribution.

13. A system for generating particular information which is at least one of three-dimensional information or intensity information of a tissue portion which can include at least one of a tissue surface or a tissue volume, comprising:
    a non-transitory computer-accessible medium having instructions thereon, wherein, when a computer arrangement executes the instructions, the computing arrangement is configured to:
    calculate a light intensity distribution of light provided on the tissue portion; use the light intensity distribution, determining one or more attenuation maps of the tissue portion;
    obtain one or more multispectral measurements of the light intensity distribution on the tissue volume taken from one or more views; and
    generate the particular information using an image reconstruction procedure in conjunction with data from the one or more tissue attenuation maps and the multispectral measurements.

14. The system of claim 13, wherein the tissue volume comprises a curved tissue surface.

15. The system of claim 14, wherein the light intensity distribution is calculated for a given set of point sources on the curved tissue surface.

16. The system of claim 13, wherein the light intensity distribution is calculated using a light propagation model.

17. The system of claim 16, wherein the light propagation model includes at least one of a radiative transfer procedure, a simplified harmonics procedure, or a diffusion procedure.

18. The system of claim 17, wherein the simplified spherical harmonics procedure includes a diffusion equation that is solved with at least one of a finite-difference procedure, a finite volume procedure, or a finite element procedure.

19. The system of claim 18, wherein the solving procedure includes using at least one of structured grids with equidistant grid points that define a domain of the tissue volume or unstructured grids with irregular grid point separations which define a domain of the tissue volume.

20. The system of claim 13, wherein the one or more attenuation maps of the tissue volume are represented by absorption and scattering coefficients of the tissue.

21. The system of claim 13, wherein the one or more attenuation maps of the tissue volume are determined by one or more of: (1) a light propagation model; (2) a global parameter optimization technique; and (3) a give source distribution.

22. The system of claim 13, wherein the computing arrangement is further configured to reconstruct a source distribution by one or more of: (1) determining a light propagation model; (2) the one or more attenuation maps of the tissue volume; and (3) a linear image reconstruction procedure.

23. The system of claim 13, wherein the information includes at least one a source power density, a source distribution in 3D space, or a concentration distribution.

24. The system of claim 13, further comprising an electromagnetic radiation source arrangement configured to provide the light.

* * * * *